(12) United States Patent
Abbasi

(10) Patent No.: US 9,789,341 B2
(45) Date of Patent: Oct. 17, 2017

(54) SYSTEM FOR ADJUSTING THE ENERGY LEVEL OF A PROTON BEAM PROVIDED BY A CYCLOTRON, A CYCLOTRON TARGET HOLDER ASSEMBLY WITH A REMOVABLE DEGRADER, A REMOVABLE DEGRADER FOR USE IN A CYCLOTRON TARGET HOLDER ASSEMBLY, AND METHODS OF USE THEREOF

(71) Applicant: NCM USA BRONX LLC, Bronx, NY (US)

(72) Inventor: Ali A. Abbasi, New York, NY (US)

(73) Assignee: NCM USA BRONX LLC, Bronx, NY (US)

( * ) Notice: Subject to any disclaimer, the term of this patent is extended or adjusted under 35 U.S.C. 154(b) by 0 days.

(21) Appl. No.: 15/253,277

(22) Filed: Aug. 31, 2016

(65) Prior Publication Data

US 2017/0062087 A1    Mar. 2, 2017

Related U.S. Application Data

(60) Provisional application No. 62/212,238, filed on Aug. 31, 2015.

(51) Int. Cl.
*A61N 5/10* (2006.01)
*G21K 1/10* (2006.01)

(52) U.S. Cl.
CPC ......... *A61N 5/1077* (2013.01); *A61N 5/1042* (2013.01); *G21K 1/10* (2013.01); *A61N 2005/1087* (2013.01); *A61N 2005/1095* (2013.01)

(58) Field of Classification Search
USPC ...................................................... 250/492.3
See application file for complete search history.

(56) References Cited

U.S. PATENT DOCUMENTS

| 2008/0078942 | A1* | 4/2008 | Rietzel | A61N 5/1043 250/396 R |
| 2014/0005463 | A1* | 1/2014 | Jongen | A61N 5/1037 600/1 |
| 2016/0067525 | A1* | 3/2016 | Bouchet | A61N 5/1049 600/1 |

\* cited by examiner

*Primary Examiner* — Kiet T Nguyen
(74) *Attorney, Agent, or Firm* — Norton Rose Fulbright US LLP; Aaron Grunberger

(57) ABSTRACT

A system for adjusting the energy level of a proton beam provided by a cyclotron includes the cyclotron and a target holder assembly including a removable degrader. The removable degrader can be removed and/or replaced without removal of the target holder assembly from the cyclotron. A method for adjusting an energy level of a proton beam of a cyclotron includes providing a target holder assembly with a removable degrader in the path of the proton beam of the cyclotron to reduce the energy level of the proton beam, where the removable degrader can be removed from the path of the proton beam without removal of the target holder assembly from the cyclotron.

16 Claims, 9 Drawing Sheets

SYSTEM FOR ADJUSTING THE ENERGY LEVEL OF A PROTON BEAM PROVIDED BY A CYCLOTRON, A CYCLOTRON TARGET HOLDER ASSEMBLY WITH A REMOVABLE DEGRADER, A REMOVABLE DEGRADER FOR USE IN A CYCLOTRON TARGET HOLDER ASSEMBLY, AND METHODS OF USE THEREOF

CROSS-REFERENCE TO RELATED APPLICATION

The present application claims the benefit, under 35 U.S.C. §119(e), of U.S. Provisional Pat. App. Ser. No. 62/212,238, filed Aug. 31, 2015, which is hereby incorporated herein by reference in its entirety.

FIELD OF THE INVENTION

The present invention relates to a system for adjusting the energy level of a proton beam provided by a cyclotron, a cyclotron target holder assembly, a removable degrader, and methods of using the same.

BACKGROUND

Particle accelerators are used to provide particle beams of charged particles. Cyclotrons commonly provide particle beams that have a fixed energy level. For example, the PETtrace 880 cyclotron manufactured by GE Healthcare (Husbyborg, Sweden) has a fixed energy of 16.5 meV. Some cyclotrons are capable of producing particle beams where the energy is variable, for example the ACS PET trace system.

SUMMARY

The cyclotrons capable of producing beams with variable energy cannot be adjusted to produce energy below 14 meV. However, there may be instances where a lower meV is desired, for example as discussed in U.S. Provisional Pat. App. Ser. No. 62/171,453, the entirety of which is incorporated by reference herein. Furthermore, commercially available cyclotron instruments allowing for variable energy are much more complicated than fixed-energy cyclotrons. These differences result in additional cost and downtime related to maintenance and repairs of variable energy cyclotrons compared to fixed-energy cyclotrons. Finally, commercially available cyclotrons having variable energy beams do not allow for independent variation of energy level at each of the targets where there is more than one target. This is because the energy of the beam is adjusted by intrinsically changing the energy level at the beam source.

The present invention provides a target holder assembly configured to hold a target material for bombardment of the target by a particle beam of a fixed-energy cyclotron including: a target body including a housing with a slot for receiving a removable degrader to place an attenuation disc of the degrader in a path of the particle beam of the cyclotron to reduce an energy level of the particle beam prior to the beam reaching the target material, wherein the degrader can be inserted into, and removed from, the target holder assembly without removal of the target holder assembly from the fixed-energy cyclotron.

According to an example embodiment of the present invention, the target body includes a first target body section separate from a second body section, the first body section being configured to hold the target material. According to an example embodiment of the present invention, the second target body section is configured to house the removable degrader. According to an example embodiment of the present invention, the target body further includes a third target body section, and the second and third target body sections are configured to attach to the fixed-energy cyclotron without attachment of the first target body section.

According to an example embodiment of the present invention, a removable degrader for use in a fixed-energy cyclotron includes a frame, an attenuation disc, a first circular channel and a second circular channel, where the first and second circular channels circumscribe the attenuation disc on respective sides of the attenuation disc, the removable degrader is configured for insertion into the cyclotron such that, when inserted, the attenuation disc is in a path of the particle beam and is configured to allow for removal and/or replacement of the attenuation disc from the path of the particle beam without removal of a target holder assembly housing the removable degrader, and the attenuation disc is configured to reduce the energy level of the particle beam that passes through the attenuation disc to reach a target.

In an example embodiment of the present invention, the removable degrader further includes a first metal O-ring within the first circular channel and a second metal O-ring within the second circular channel.

According to an example embodiment of the present invention, a target holder assembly for use in a fixed-energy cyclotron includes a body and a removable degrader according to any one of the above embodiments, where the removable degrader can be fitted into the body of the target holder assembly to place an attenuation disc in a path of the particle beam, and can be removed and/or replaced from the body of the target holder assembly without removal of the target holder assembly from the fixed-energy cyclotron, and the attenuation disc is configured to reduce the energy level of the particle beam that reaches a target.

In an example embodiment, the body includes a first target body, a second target body, a third target body, where the first target body is configured to hold a target material, the second target body is configured to house a removable degrader, and the second and third target bodies are configured to attach to the fixed-energy cyclotron without attachment of the first target body.

The present invention also provides a removable degrader for use in a fixed-energy cyclotron including a frame; an attenuation disc; a first circular channel at a first side of the attenuation disc and a second circular channel at a second side of the attenuation disc; wherein the first and second circular channels circumscribe the attenuation disc; the removable degrader is configured for removable insertion of the degrader into a target holder, without removal of the target holder from the fixed cyclotron and so that, when the removable degrader is removably inserted into a target holder, the attenuation disc is positioned in a path of a particle beam, thereby reducing an energy level of the particle beam before the particle beam reaches a target held by the target holder; and the target holder into which the removable degrader is adapted to be inserted includes a first housing section with a slot for receiving the removable degrader and a second housing section that is configured to hold the target and to be shifted towards the first housing section to form an air tight seal of the attenuation disc of the degrader, when the degrader is positioned in the slot. According to an example embodiment of the present invention, the removable degrader further includes a first metal O-ring within the first circular channel and a second metal O-ring within the second circular channel.

The present invention also provides a system for adjusting the energy level of a particle beam provided by a fixed-energy cyclotron, the system including the fixed-energy cyclotron and a target holder assembly according to any one of the above target holder assemblies.

The present invention also provides a method for reducing an energy level of a particle beam of a fixed-energy cyclotron, the method including providing a target holder assembly with a removable degrader in the path of the particle beam of the fixed-energy cyclotron, where the removable degrader is configured to be removed and/or replaced without removal of the target holder assembly from the cyclotron.

The present invention also provides a method for independently reducing an energy level of particle beams reaching at least two targets of a fixed-energy cyclotron, the method including providing two or more target holder assemblies each with a removable degrader in the path of the particle beam of the fixed-energy cyclotron before their respective targets, where each removable degrader includes an attenuation disc, the thickness of each removable degrader is independently selected, and each of the removable degraders is configured to be removed and/or replaced without removal of its respective target holder assembly from the cyclotron.

These and other embodiments of the invention will be better appreciated and understood when considered in conjunction with the following description and the accompanying drawings. However, the following description, while indicating various embodiments of the invention and numerous specific details thereof, is given by way of illustration and not of limitation. Many substitutions, modifications, additions and/or rearrangements can be made within the scope of the invention without departing from the spirit thereof, and the invention includes all such substitutions, modifications, additions and/or rearrangements.

The drawings accompanying and forming part of this specification are included to depict certain aspects of the invention. A clearer conception of the invention and of the components and operation of systems provided with the invention will become more readily apparent by referring to the exemplary, and therefore non-limiting, embodiments illustrated in the drawings, where like reference numerals (if they occur in more than one view) designate the same or similar elements. The invention may be better understood by reference to one or more of these drawings in combination with the description presented herein. The features illustrated in the drawings are not necessarily drawn to scale.

DETAILED DESCRIPTION

Figure 1:
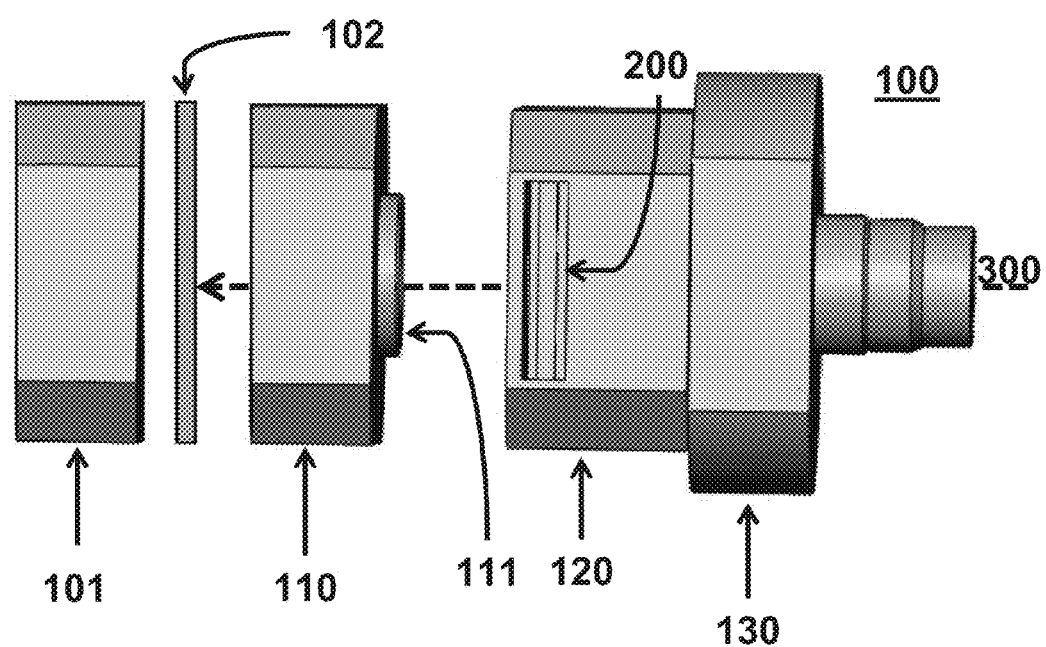
FIG. 1 shows an exploded side view of a schematic illustrating a target holder assembly according to an example embodiment of the present invention for a solid target with a removable degrader placed inside a degrader receiving window.

Example embodiments of the present invention provide a cyclotron system, a target holder assembly, a removable degrader, and methods of use thereof that allow for adjusting the energy level of a fixed-energy cyclotron beam. According to an example embodiment of the present invention, a cyclotron system includes a target holder assembly, a removable degrader, and a fixed-energy cyclotron, where the energy level of the proton beam of the fixed-energy cyclotron is adjusted by providing a removable degrader into the path of the proton beam in a target holder assembly. According to an example embodiment of the present invention, the cyclotron system includes multiple targets, where the energy of the proton beam is independently adjusted for each target by independently providing a removable degrader including an attenuation disc with a respective thickness (or material) for each target holder assembly of the fixed-energy cyclotron. According to an example embodiment of the present invention, the target holder assembly and the removable degrader are configured to allow for removal and/or replacement of the removable degrader from the path of the proton beam without removal of the target holder assembly from the cyclotron. According to an example embodiment of the present invention, the energy level of the proton beam produced by the fixed-energy cyclotron is adjusted by replacing a removable degrader including a first thickness (or material) with another removable degrader including a second thickness (or material). A method, according to an example embodiment of the present invention, of adjusting the beam energy using the removable degrader, substantially reduces the adjustment time by advantageously doing away with the need for powering down the cyclotron, removing the target holder assembly, reassembling the target holder assembly, and powering on the cyclotron. By allowing for the removable degrader to be removed and/or replaced from the body of the target holder assembly without removal of the target holder assembly from the fixed-energy cyclotron, the cyclotron is able to remain powered on and in particular the vacuum created by the cyclotron is maintained to decrease the downtime of the cyclotron. The method, according to an example embodiment of the present invention, of adjusting the beam energy using the removable degrader, advantageously reduces the resulting exposure of service personnel to radiation thereby increasing operating safety. The compact design of the target holder assembly, according to an embodiment of the present invention, allows for a direct bolt-on replacement of conventional target holder assemblies without the need for additional modification to the cyclotron.

Cyclotrons are generally used to irradiate target materials with a proton beam in order to cause a nuclear reaction in the target material. For example, commercially available proton beam cyclotrons such as the PETtrace 880 cyclotron manufactured by GE Healthcare (Husbyborg, Sweden), can be used to create radioisotopes. The target material can be liquid, gas, foam, or solid. The target material is held or contained in a target holder assembly using the appropriate assembly configuration for the target material type.

In an example embodiment, a fixed-energy cyclotron is provided with a configuration that facilitates reduction of the energy level of the proton beam from its factory setting. FIG. 1 shows a target holder assembly 100 and removable degrader 200 according to an example embodiment present invention. In an example embodiment, the target holder assembly includes a first target body 110, a second target body 120, and a third target body 130. The third target body 130 is configured to mate with a housing of the cyclotron (not shown). This particular target holder assembly 100 is configured for irradiating a solid target 102. However, the target holder assembly 100 can be modified by replacing solid target components 101, 102, and 110 with a modified first target body that is configured for a liquid, gas, or foam target.

Figure 2:
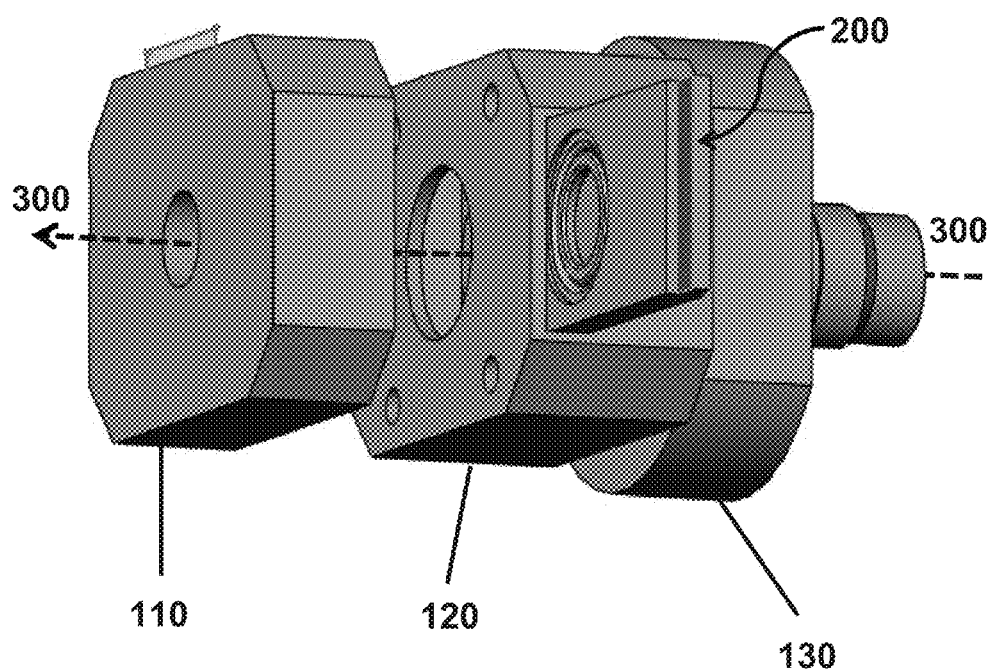
FIG. 2 shows a first exploded perspective view of a schematic illustrating the target holder assembly, according to an example embodiment of the present invention, with a generalized first target body and with the removable degrader pulled out of the degrader receiving window.
Figure 3:
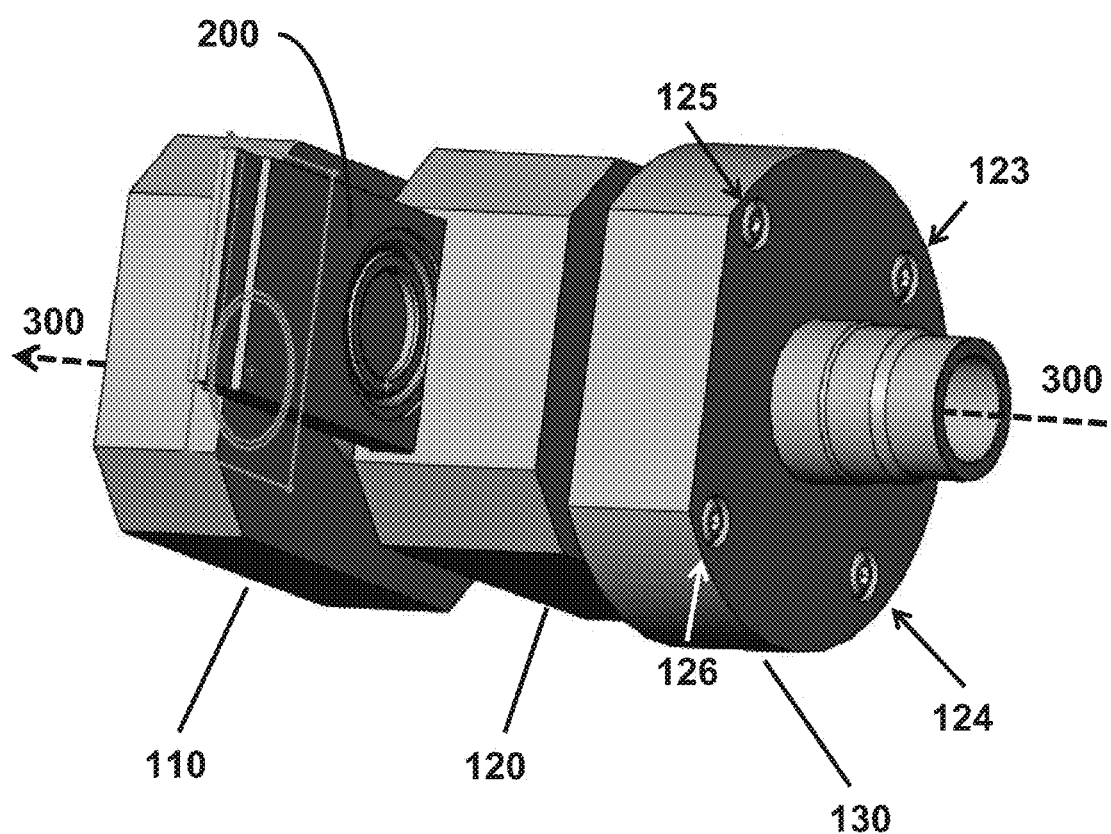
FIG. 3 shows a second exploded perspective view of the schematic illustrating the target holder assembly of FIG. 2, according to an example embodiment of the present invention.

In an example embodiment, as shown in FIGS. 2 and 3, the target holder assembly 100 allows for the second target body 120 and third target body 130 to be attached to the cyclotron housing independently from the first target body 110 (which includes the target material, outlined in the figure, and is to be bombarded by the proton beam). This allows for the pressure between the first target body 110 and the second target body 120 to be adjusted independently from the pressure supplied between the second target body 120 and third target body 130 and independently from the pressure supplied between the third target body 130 and the cyclotron housing. For example, the pressure between the first target body 110 and the second target body 120 may be provided by a pneumatic system (not shown). The pressure applied by the pneumatic system is independent from the means of providing pressure between the second target body 120 and the third target body 130, as well as the pressure between the third target body 130 and the cyclotron housing (not shown). The vacuum foil 131 between the second target body 120 and the third target body 130 allows for negative pressure to be created inside the chamber of the third target body 130 by a vacuum generated by the cyclotron. During normal operation the cyclotron provides enough of a vacuum to generate a deep space vacuum ($10^{-6}$ to $<3\times10^{-17}$ Torr). The negative pressure provided by this vacuum is sufficient to maintain attachment of the third target body 130 to the cyclotron housing. The third target body 130 may alternatively or additionally be attached to the cyclotron housing by mechanical means known in the art. The second target body 120 may be attached to the third target body 130 by mechanical means known in the art, for example using bolts 123-126. In this example configuration, the second target body 120 and third target body 130 remain attached to the cyclotron housing at least due to the vacuum being generated by the cyclotron. In this manner, the pressure applied upon the removable degrader 200 by the first target body 110 can be adjusted to allow for removal and/or replacement of the removable degrader 200 without removal of the target holder assembly 100. Therefore, by reducing only the pressure applied on the removable degrader 200 by the first target body 110, the removable degrader 200 may be removed and/or replaced with another removable degrader that includes an attenuation disc having a different thickness (or material), without needing to disassemble and/or remove any of the target bodies.

Figure 4:
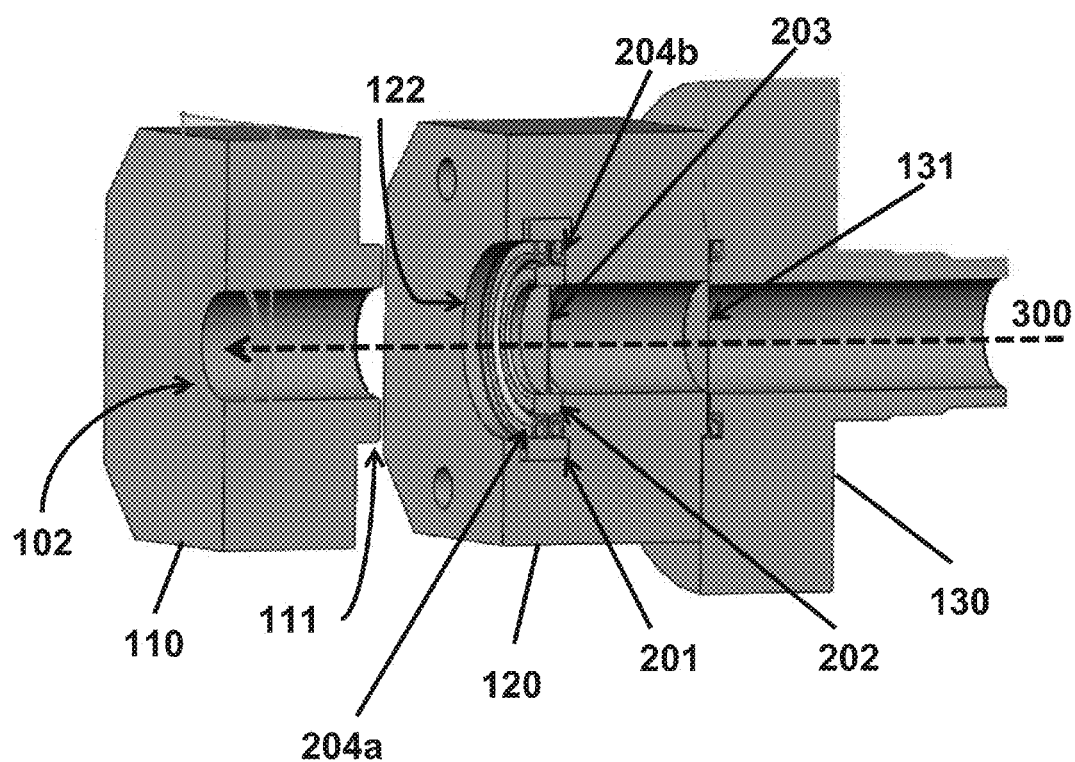
FIG. 4 shows an exploded cross-sectioned perspective view of a schematic illustrating the target holder assembly, according to an example embodiment of the present invention.

FIG. 4 shows the position of the attenuation disc 203, which is part of the removable degrader 200, when introduced into the beam path 300. The surface of the attenuation disc 203 is perpendicular to the beam path 300 in order to reduce the MeV of the cyclotron. The first target body 110 can be tightened to press lip 111, which is inserted into bore 122 of target body 120, against metal O-ring 204a, which provides pressure to the removable degrader 200 and the other metal O-ring 204b. This results in an air tight seal around the attenuation disc 203, so that the cyclotron can then be activated to provide a positive pressure flow of cooled helium gas to both sides of the attenuation disc 203 without gas leakage.

Figure 5:
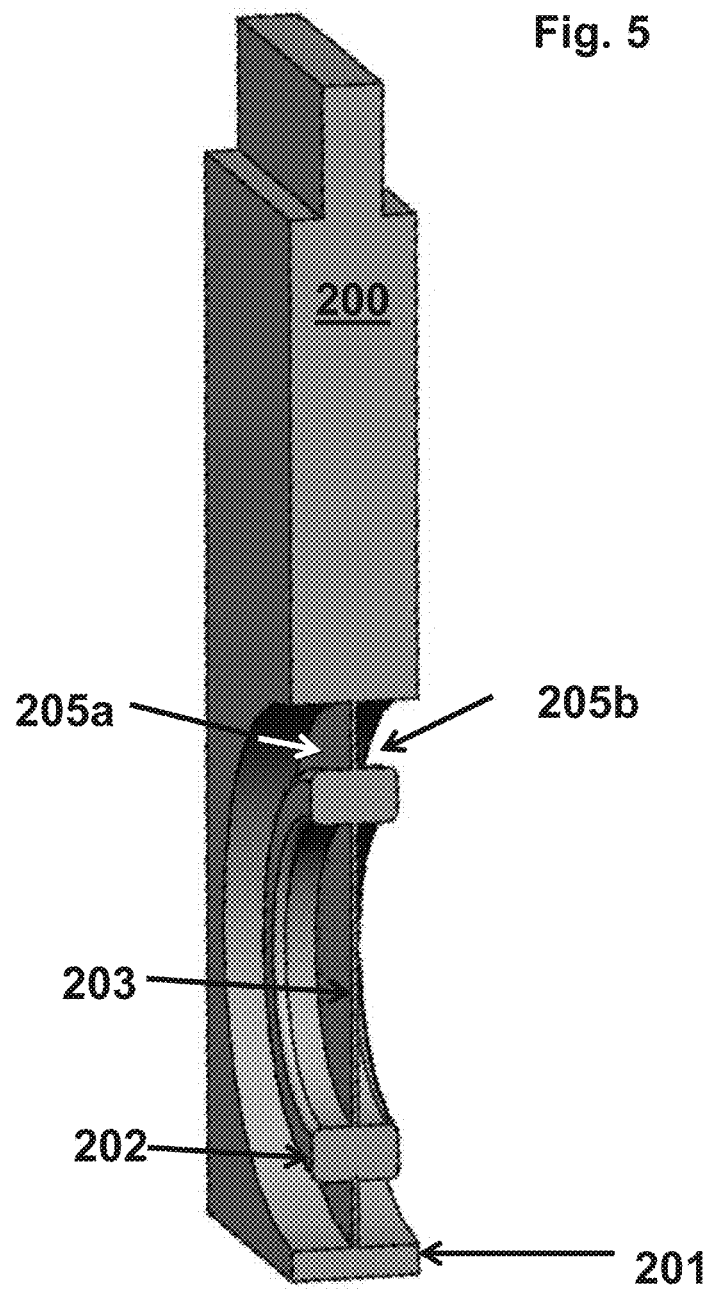
FIG. 5 shows a cross-sectioned perspective view of a schematic illustrating the removable degrader, according to an example embodiment of the present invention.

In FIG. 5, a cross section view of the removable degrader 200 is shown. The removable degrader 200 includes a frame 201 that surrounds an attenuation disc 203 and two O-ring channels 205a, 205b that hold and support metal O-rings 204a, 204b between concentric lips of the O-ring channels 205a, 205b provided by the frame 201 and inner ring 202. The frame 201 and the attenuation disc 203 can be made from distinct components or fabricated as a single integral piece. Preferably, the entire removable degrader is made from a single piece of aluminum. Preferably, a thickness of the attenuation disc 203 is uniform and depends on the desired level of beam energy reduction. In an example embodiment, the attenuation disc 203 is cooled by a flow of cooled helium gas on both surfaces of the attenuation disc 203 to minimize production of byproducts and other impurities.

Figure 6:
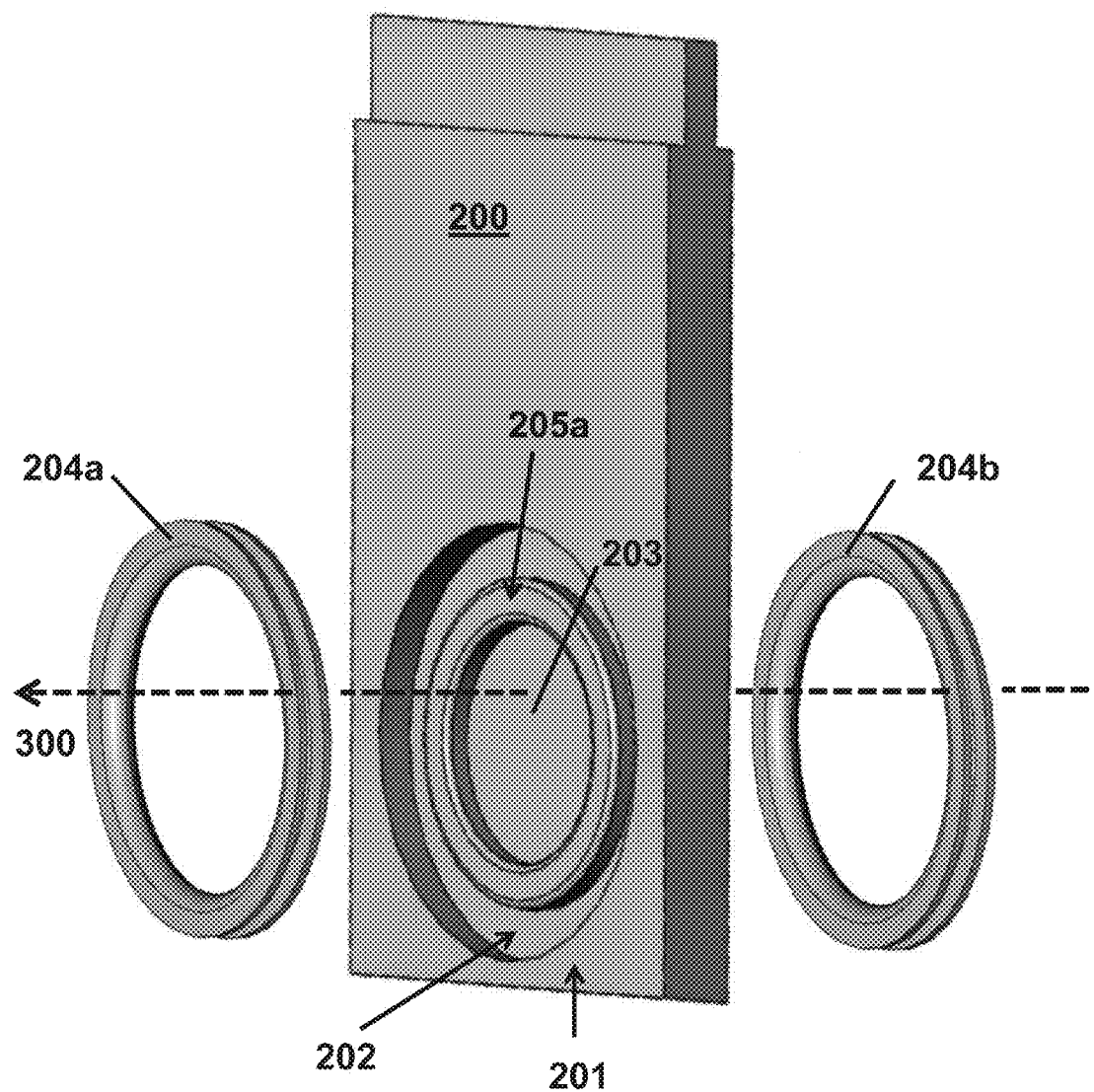
FIG. 6 shows an exploded perspective view of a schematic illustrating the removable degrader along with its accompanying metal O-rings, according to an example embodiment of the present invention.

In FIG. 6, the configuration of the metal O-rings 204a, 204b and the O-ring channel(s) 205a (and 205b) are shown. The removable degrader 200 and metal O-rings 204a, 204b are structured for insertion in the second target body 120 so that the attenuation disc 203 is between the vacuum foil 131 and the target material 102 in the beam path (as shown in FIG. 4). A vacuum is then created in a beam channel along the beam path 300 upstream of the vacuum foil 131 with respect to the beam flow direction 300. Using the removable degrader 200, the energy of the provided proton beam downstream of the attenuation disc 203 is adjusted, prior to reaching the target material, from the default setting.

In an example embodiment, the thickness of the attenuation disc 203 in the removable degrader is about 0.6 to 0.9 mm and is used to reduce the energy to about 11-12 MeV from the factory default energy level of 16.5 MeV.

Figure 7:
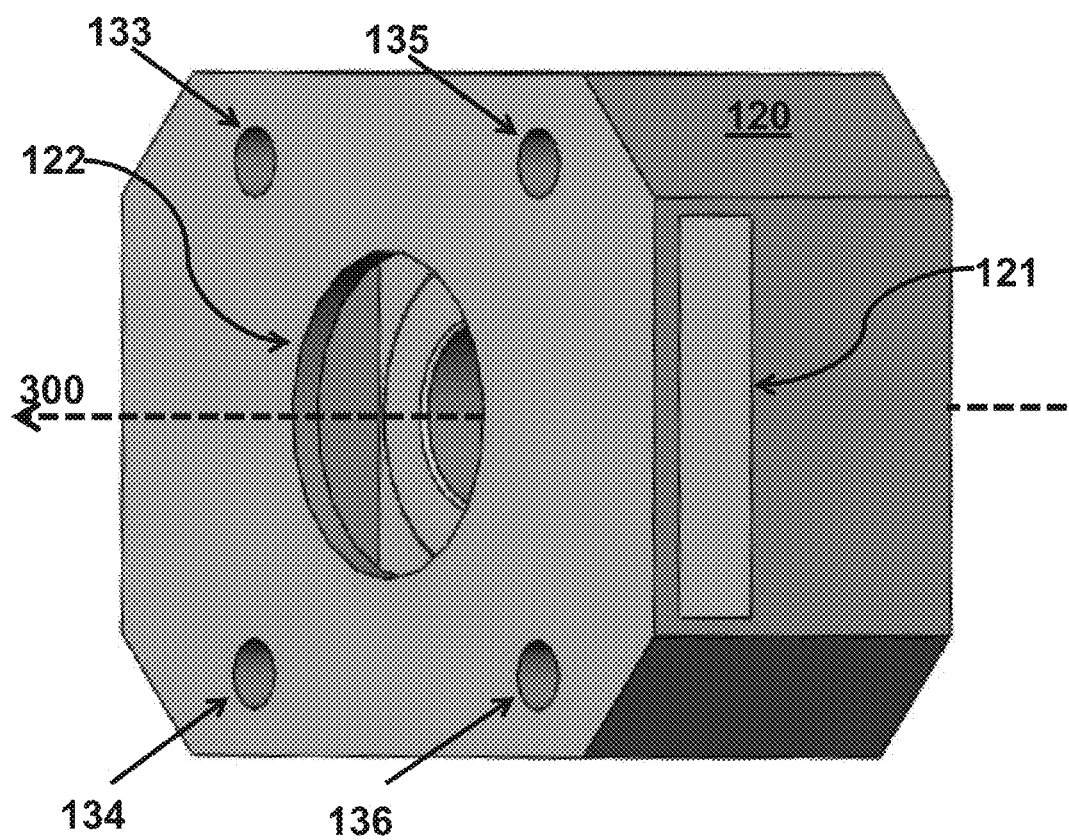
FIG. 7 shows a schematic illustrating a second target body portion of the target holder assembly, without the removable degrader, according to an example embodiment of the present invention.
Figure 8:
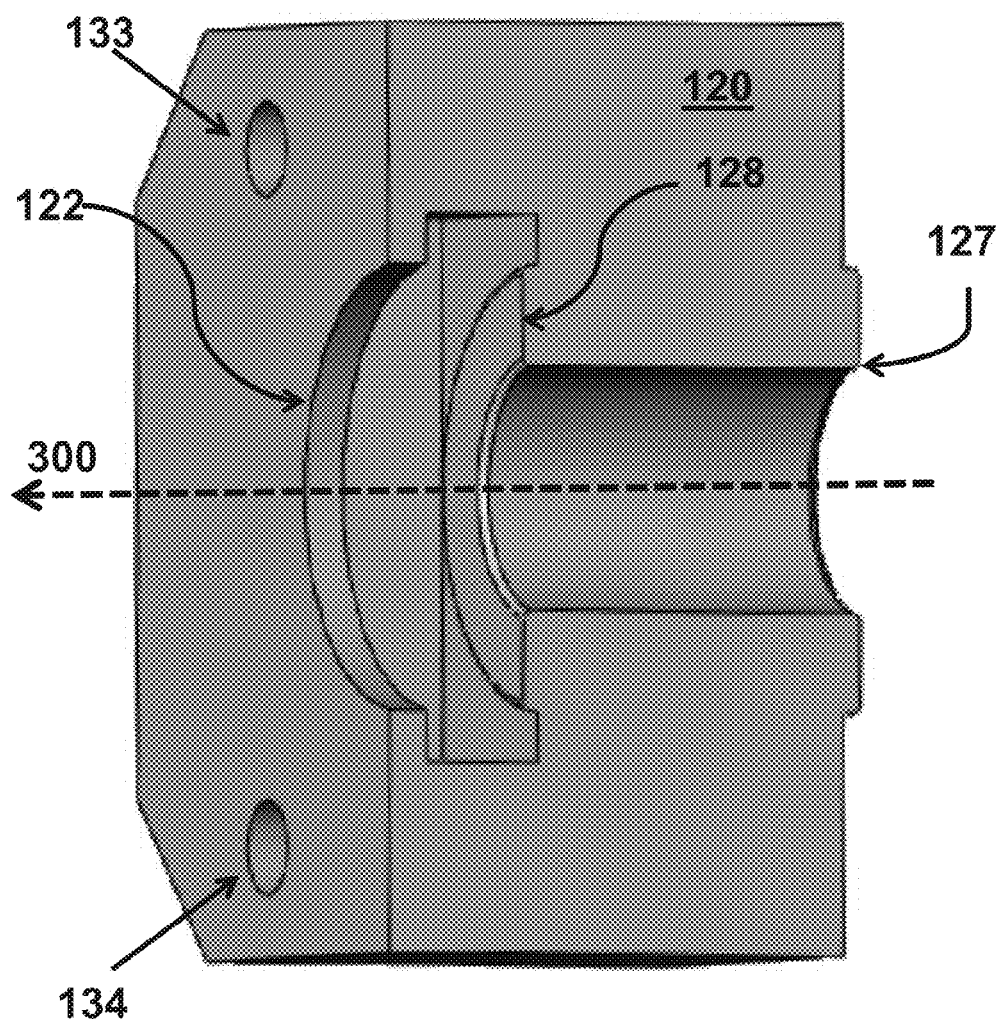
FIG. 8 shows a cross-sectional perspective view of a schematic illustrating the second target body without the removable degrader.
Figure 9:
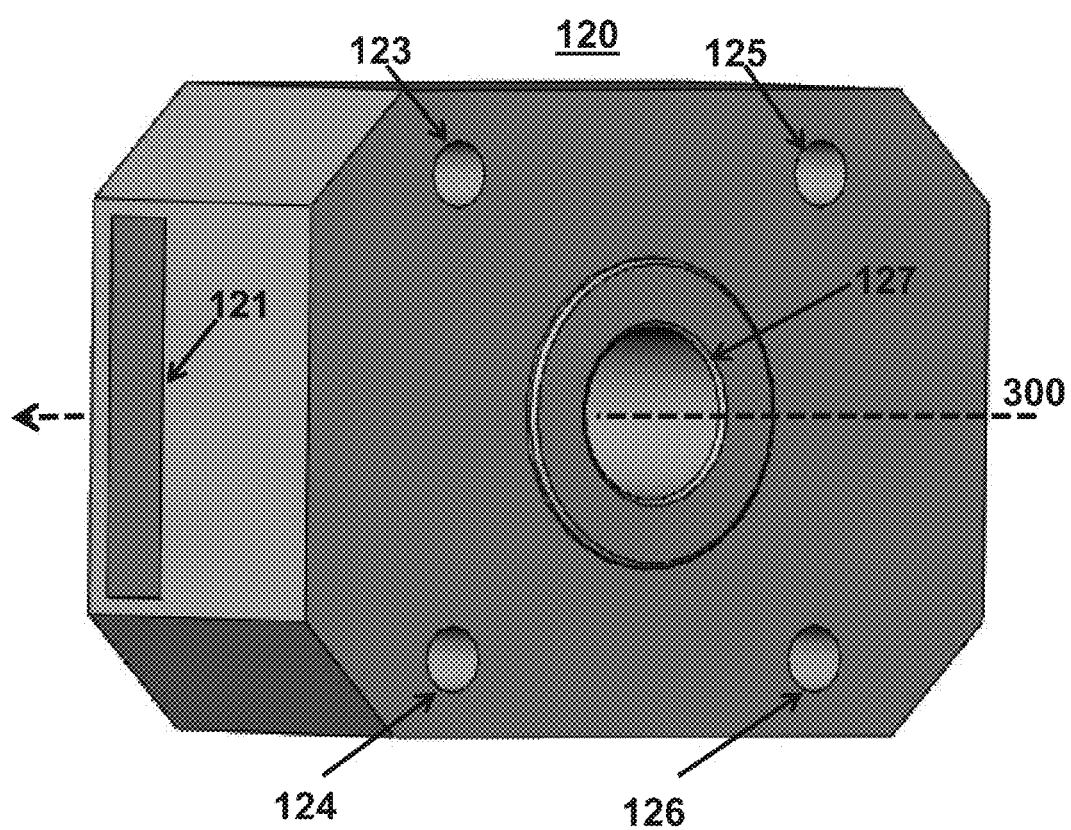
FIG. 9 shows another perspective view of the schematic illustrating the second target body without the removable degrader.

FIGS. 7 to 9 show the second target body 120 without the removable degrader 200. A receiving window 121 is structured for an accurate fit and alignment of the frame 201 of removable degrader 200 in second target body 120. Channels 133-136 are provided to allow for connection of the second target body 120 to the third target body 130 for example using bolts 123-126, or other affixation components. Raised ridge 128 is provided to contact metal O-ring 204b to provide an air tight seal once sufficient pressure is applied.

The present invention is not limited to only the PETtrace 880 cyclotron, but can be equally implemented using other cyclotron models to provide reduced beam energies. Fixed-energy accelerators can be modified by introducing degraders into the pathway of the proton beam. The degraders, in example embodiments of the present invention, work according to the principle according to which any particle passing through a block of material undergoes a decrease in its energy by an amount which is, for particles of a given type, a function of the thickness and/or intrinsic characteristics of the material through which the particle passes. Therefore, the energy of the beam can also be adjusted to other energy levels by, for example, changing the thickness of the energy attenuation disc because the greater the thickness of the energy attenuation disc, the greater the reduction in energy. In an embodiment, the energy level of the beam is reduced using the removable degrader by about 0.5 MeV to about 8 MeV. In another embodiment, the energy level of the beam is reduced using the removable degrader by about 3 MeV to 7 MeV. In an embodiment, the energy level of the beam is reduced using the removable degrader by about 5 MeV. In one embodiment, a beam current of at least 30-60 µA is used.

Example

A PETtrace 880 cyclotron was modified using a target holder assembly and removable degrader according to an example embodiment of the present invention. The energy attenuation disc was placed in the proton beam path, downstream of a vacuum foil of a solid target, and upstream of the target material. The removable degrader had a 0.6 mm thick aluminum attenuation disc in order, and reduced the MeV of the GE PETtrace 880 from 16.5 MeV to about 11-12 MeV at the target.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following.

What is claimed is:

1. An assembly for a fixed-energy cyclotron, wherein the cyclotron is configured to produce a particle beam, the assembly comprising:
a target holder assembly comprising a target body that includes:
a first region configured to hold a target material;
a second region with a receiving slot; and
a third region including a receiving section for receiving the particle beam from the cyclotron; and
a removable degrader comprising an attenuation disc;
wherein:
the receiving slot is configured to receive the removable degrader;
the removable degrader is configured for removable insertion into the receiving slot such that, when (a) the removable degrader is in the receiving slot, (b) the target material is held in the first region of the target body, and (c) the particle beam travels into the receiving section, the attenuation disc is positioned in a path of the particle beam that extends from the receiving section to the target material; and
the attenuation disc is configured to reduce an energy level of the particle beam prior to the particle beam reaching the target material.

2. The assembly of claim 1, wherein the target holder assembly and the removable degrader are configured to allow for removal of the removable degrader without removal of the target holder assembly from the cyclotron.

3. The assembly of claim 1, wherein:
the target body includes a first target body in which the first region is located, a second target body in which the second region is located, and a third target body in which the third region is located; and
the second target body and the third target body are configured to attach to the cyclotron independently from the first target body, to allow a pressure between the first target body and the second target body to be adjusted independently from a pressure between the second target body and the third target body, and from a pressure between the third target body and the cyclotron.

4. The assembly of claim 3, wherein the first target body is configured to shift towards the second target body when the removable degrader is inserted into the receiving slot to form an air tight seal around the attenuation disc.

5. The assembly of claim 3, wherein the target holder assembly further comprises a vacuum foil between the second target body and the third target body, and wherein the attenuation disc is positioned between the vacuum foil and the target material when the removable degrader is inserted into the receiving slot.

6. The assembly of claim 1, wherein:
the removable degrader further comprises:
a frame;
an inner ring;
a first circular channel formed by the inner ring and the frame at a first side of the attenuation disc;
a second circular channel formed by the inner ring and the frame at a second side of the attenuation disc;
a first O-ring within the first circular channel; and
a second O-ring within the second circular channel; and
the first and second circular channels circumscribe the attenuation disc.

7. The assembly of claim 1, wherein the removable degrader is made from a single piece of aluminum.

8. The assembly of claim 1, wherein a thickness of the attenuation disc is about 0.6 to 0.9 mm.

9. The assembly of claim 8, wherein the thickness of the attenuation disc is uniform.

10. A method of adjusting an energy level of a particle beam of a fixed-energy cyclotron prior to the particle beam reaching a target material, the method comprising:
inserting a removable degrader with an attenuation disc into a receiving slot of a target holder assembly, wherein:
the removable degrader is configured for removable insertion into the receiving slot such that, when inserted, the attenuation disc is positioned in a path of the particle beam that extends from the cyclotron to the target material, and
the attenuation disc is configured to adjust the energy level of the particle beam prior to the particle beam reaching the target material.

11. The method of claim 10, wherein the target holder assembly and the removable degrader are configured to allow for removal of the removable degrader without removal of the target holder assembly from the cyclotron.

12. The method of claim 11, wherein the attenuation disc is configured to reduce the energy level of the particle beam.

13. The method of claim 12, further comprising:
removing the removable degrader from the receiving slot without removing the target holder assembly from the cyclotron; and
inserting a second removable degrader with a second attenuation disc into the receiving slot;
wherein:
the second removable degrader is configured for removable insertion into the receiving slot such that, when inserted, the second attenuation disc is positioned in the path of the particle beam, and
the second attenuation disc has a thickness that is different than a thickness of the attenuation disc.

14. A method of independently adjusting energy levels of first and second particle beams of a cyclotron prior to the particle beams reaching their respective first and second target materials, the method comprising:
(a) inserting a first removable degrader with a first attenuation disc into a first receiving slot of a first target holder assembly; and
(b) inserting a second removable degrader with a second attenuation disc into a second receiving slot of a second target holder assembly;
wherein the first and second removable degraders are configured for removable insertion into the respective first and second receiving slots such that, when inserted, the respective first and second attenuation discs are positioned in respective paths of the first and second particle beams that extend from the cyclotron to the respective first and second target materials.

15. The method of claim 14, wherein the first attenuation disc has a first thickness and the second attenuation disc has a second thickness, and wherein the first thickness and second thickness are different.

16. The method of claim 14, wherein the first and second target holder assemblies and the first and second removable degraders are configured to allow for removal of the first and second removable degraders without removal of the first and second target holder assemblies from the cyclotron.

* * * * *